United States Patent
Ruhr et al.

(10) Patent No.: US 6,719,891 B2
(45) Date of Patent: Apr. 13, 2004

(54) POINT-OF-USE GENERATION OF CHLORINATED ALKALINE CLEANING SOLUTIONS BY ELECTROLYSIS

(75) Inventors: Richard Ruhr, Buffalo, MN (US); Nathan Peitersen, Richfield, MN (US); Joel Schilling, South St. Paul, MN (US); Harold Matson, White Bear Lake, MN (US); Sara Peters, Apple Valley, MN (US); Bryan Anderson, St. Paul, MN (US); Mike Shulman, Minneapolis, MN (US); Paul Pankratz, Lakeville, MN (US)

(73) Assignee: Ecolab Inc., St. Paul, MN (US)

( * ) Notice: Subject to any disclaimer, the term of this patent is extended or adjusted under 35 U.S.C. 154(b) by 28 days.

(21) Appl. No.: 09/990,134

(22) Filed: Nov. 21, 2001

(65) Prior Publication Data

US 2003/0098244 A1 May 29, 2003

(51) Int. Cl.⁷ .............................. C02F 1/461; C25B 1/26
(52) U.S. Cl. ....................... 205/500; 205/620; 205/687
(58) Field of Search ............................... 205/500, 620, 205/687

(56) References Cited

U.S. PATENT DOCUMENTS

| | | | |
|---|---|---|---|
| 3,797,744 A | 3/1974 | Smith | 239/172 |
| 4,691,840 A | 9/1987 | Ferbrache | 220/318 |
| 4,839,003 A | 6/1989 | Dworak et al. | 204/98 |
| 4,941,596 A | 7/1990 | Marty et al. | 222/144.5 |
| 4,976,137 A | 12/1990 | Decker et al. | 73/53 |
| 5,014,211 A | 5/1991 | Turner et al. | 364/478 |
| 5,154,806 A | 10/1992 | Prevost | 204/99 |
| 5,203,366 A | * 4/1993 | Czeck et al. | 137/3 |
| 5,367,283 A | 11/1994 | Lauf et al. | 338/34 |
| 5,567,283 A | 10/1996 | Lynn et al. | 204/228 |
| 5,616,234 A | * 4/1997 | Rhees et al. | 205/500 |
| 5,688,385 A | 11/1997 | Rhees et al. | 204/237 |
| 5,746,238 A | 5/1998 | Brady et al. | 137/3 |
| 5,779,874 A | 7/1998 | Lemke | 205/334 |
| 5,967,202 A | 10/1999 | Mullen et al. | 141/104 |
| 6,217,741 B1 | 4/2001 | Doi | 205/620 |

OTHER PUBLICATIONS

Kirk–Othmer's Encyclopedia of Chemical Technology, Third Edition, vol. 1, pp. 799–865 and vol. 8, pp. 662–694., (no date).

Baker, R. J., Types and Significance of Chlorine Residuals, Journal of American Water Works Association, 1959 (51:1185), pp. 472–473., no month.

White, G. C., Handbook of Chlorination, 4th Edition, John Wiley & Sons, Inc., 1999, p 1503., no month.

* cited by examiner

Primary Examiner—Arun S. Phasge
(74) Attorney, Agent, or Firm—Vidas, Arrett & Steinkraus (57) ABSTRACT

An on-site apparatus and method for preparing aqueous cleaning compositions, including an electrolytic cell for producing and dispensing chlorine and sodium hydroxide for use in various cleaning and/or sanitizing formulations at the point of use.

30 Claims, 7 Drawing Sheets

Figure 1: Electrolytic Membrane Cell

Figure 2

Figure 3: On-site HOCl Generation

Figure 4

Figure 5: On-site NaOH/NaOCl Generation

POINT-OF-USE GENERATION OF CHLORINATED ALKALINE CLEANING SOLUTIONS BY ELECTROLYSIS

FIELD OF THE INVENTION

The present invention relates to an on-site apparatus and method for preparing aqueous cleaning compositions, including an electrolytic cell for producing and dispensing chlorine and sodium hydroxide for use in various cleaning and/or sanitizing formulations at the point of use.

BACKGROUND OF THE INVENTION

Multi-component aqueous cleaning compositions are widely used in large scale industrial operations. The chemical manufacturing industry has traditionally employed large scale processes to manufacture either concentrated or dilute aqueous cleaners which are then shipped to the customers' use locations.

Shipment of dilute aqueous compositions involves the movement of large volumes of products which are predominantly water. Transporting large quantities of a product which is mostly water is not cost-effective.

It was recognized that significant savings in transportation expenses could be achieved if concentrated chemical compositions were shipped to the use location, and then diluted, rather than transporting the diluted use solutions.

However, transportation, handling, and storage of concentrated chemical compositions can be quite hazardous.

It has therefore become more popular for manufacturers of cleaning and sanitizing compositions to provide methods which enable their consumers to manufacture diluted aqueous cleaning and/or sanitizing compositions at the point at which they are used which is referred to in the industry as "point-of-use" generation of chemical cleaning and/or sanitizing compositions. These methods typically employ some apparatus which prepares a variety of cleaning compositions from chemical concentrate vessels and a water supply. These devices are often microprocessor controlled so the end use chemical recipe(s) can be programmed into the device by the supplier of the chemical concentrates. In this fashion, chemical compositions can be tailor made for specific customers and for specific end uses thereby filling a variety of needs in a simple and cost-effective manner. Examples of such dispensers include U.S. Pat. No. 3,797,744, U.S. Pat. No. 4,691,840, U.S. Pat. No. 4,941,596, U.S. Pat. No. 4,976,137, U.S. Pat. No. 5,014,211, U.S. Pat. No. 5,203,366 and so forth.

However, these methods still require transportation of chemical concentrates, which in some cases, can be hazardous.

For instance, chlorine is a commonly used disinfectant. Chlorine gas is manufactured almost exclusively in combination with sodium hydroxide by the electrochemical reduction of salt brine solutions using one of three methods including the membrane cell, the diaphragm cell, and the mercury cell methods. This electrochemical process for producing chlorine in large chlorine/caustic plants using complex cells which keep the products from the anode separate from the products of the cathode is a well known art (see Kirk-Othmer's Encyclopedia of Chemical Technology, Third Edition, volume 1, pages 799–865 and volume 8, pages 662–695, which are incorporated by reference). The electrolytic reaction produces chlorine and sodium hydroxide as co-products, and produces hydrogen gas as a by-product. The production of chlorine is typically accomplished in large facilities located near an economical source of power with NaCl as principle source of chlorine.

The problem is, however, at ambient temperature and pressure, chlorine is a hazardous, toxic, heavy gas which does not disperse readily if released accidentally into the atmosphere. Therefore, once chlorine has been collected, it is cooled and compressed and placed in heavy steel cylinders for transportation to the site of use. The hazards of chlorine in gas form require rigid regulation for packaging, handling and transport. Furthermore, the danger of its escaping from the cylinders remains a possibility. In extreme situations the concern over the possible accidental release of chlorine has resulted in the prohibition of the transport of chlorine through the streets of some communities, thus preventing the use of chlorine for some of its essential uses.

The problems of storing and transporting chlorine have been minimized in some instances by venting the chlorine from the chlorine/caustic plant with the co-produced sodium hydroxide to make sodium hypochlorite which can then be transported to the site of use. The concentration of sodium hypochlorite generally is in the range of about 15% by weight. While sodium hypochlorite (NaOCl) retains several of the useful properties of chlorine (e.g., disinfection, sanitation, odor control), it also increases the cost of transport since it contains almost 85% water, is unstable, and decays with time. Salt and excess caustic from the preparation of sodium hypochlorite are contaminating by-products transferred to the system being treated.

SUMMARY OF THE INVENTION

The present invention relates to an apparatus and method for producing aqueous cleaning compositions at the point of use, including an electrolytic cell for producing chlorine and sodium hydroxide directly at the site where they are intended to be used. The chlorine and sodium hydroxide may be combined with various chemical compositions to produce cleaning and/or sanitizing compositions at the point of use.

More particularly, the present invention relates to an apparatus and method for generating cleaning compositions at the point of use including a dispensing system for mixing a plurality of chemical compositions according to a predetermined recipe by providing at least one of a concentrated chemical composition such as a buffer, a surfactant, a solvent or a water conditioning agent and combining the concentrated chemical composition with chlorine, sodium hydroxide, or mixture thereof. The process includes an on-site generator of chlorine and sodium hydroxide by electrolysis of a sodium chloride solution.

Even more particularly, the present invention includes an apparatus and method for the preparation of multi-component chemical cleaning compositions at the point of use comprising at least one electrolytic cell for generating at least one of chlorine, sodium hydroxide or mixture thereof, a plurality of concentrated chemical compositions in a plurality of vessels, each vessel storing one of said plurality of concentrated chemical compositions, a controller for selecting a predetermined amount of at least one of a plurality of concentrated chemical compositions, and a delivery system in communication with the controller. The delivery system delivers a predetermined amount of at least one of sodium hydroxide, chlorine, or mixture thereof and a predetermined amount of at least one of a plurality of chemical concentrates to a common vessel.

The dispensing system may include a computer system such that the entire process is automatic, or it may involve an on/off system in which an operator starts and stops the system by pushing a button.

The apparatus may be used to prepare dilute aqueous chemical compositions, as well as concentrates without added water. The hazards associated with the transport and storage of large quantities of liquefied chlorine under pressure, and the need for transporting concentrated sodium hydroxide, are thus eliminated.

DETAILED DESCRIPTIONS OF THE PREFERRED EMBODIMENTS

The device and method of the present invention includes an electrolytic cell for generation of chlorine and sodium hydroxide electrolytically according to the following general reaction:

$$2NaCl+2H_2O \rightarrow Cl_2+H_2+2\ NaOH$$

Figure 1:
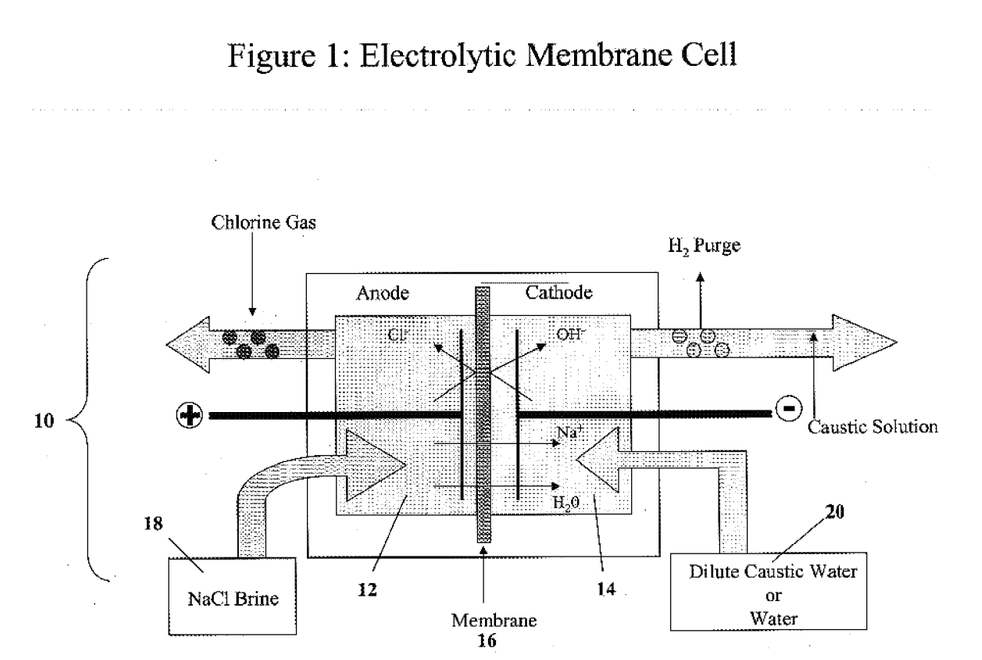
FIG. 1 illustrates an electrolytic cell which may be used in accordance with the present invention.

FIG. 1 illustrates generally at 10, an example of an electrolytic cell useful in the present invention. Electrolytic cell, 10, has an anolyte (the electrolyte at the anode compartment 12 and a catholyte (the electrolyte at the cathode) compartment 14, with a membrane 16 such as an ion-exchange membrane, i.e. cation-exchange membrane, separating the two compartments 12, 14. An electrolyte, i.e. a brine solution 18 is fed to the anode chamber 12 and dilute caustic soda or water is supplied to the cathode chamber 14 via a pumping or injecting mechanism 20.

The brine solutions typically have an alkali metal chloride such as potassium or sodium chloride, for instance, and are typically purified containing somewhere between about 20–30% of the alkali chloride. Upon direction of a current through the electrolyte, chlorine is formed at the anode which is typically graphite or a ruthenium-titanium oxide coated titanium dimensionally stable anode, and sodium hydroxide and hydrogen are formed at or near the cathode in the catholyte. Sodium hydroxide is formed when the sodium ion combines with the hydroxide ion in the cathode compartment 14.

Various types of cells can be utilized to keep the products from the anode separate from the products of the cathode. Such cells are described in, for instance, *Kirk-Othmer's Encyclopedia of Chemical Technology*, Third Edition, volume 1, pages 799–865 and volume 8, pages 662–695, incorporated by reference herein.

Examples of methods and cell types useful in the electrolytic production of chlorine and sodium hydroxide include, for instance, a diaphragm cell process, a bipolar diaphragm cell process, a membrane cell process, a mercury cell process, and so forth. Such methods and devices are known to those of skill in the art.

Examples of devices suitable for use herein are described in U.S. Pat. No. 4,976,137, U.S. Pat. No. 4,839,003, U.S. Pat. No. 5,203,366, U.S. Pat. No. 5,567,283, U.S. Pat. No. 5,779,874, and so forth, all of which are incorporated by reference herein in their entirety. An example of a mercury cell for use in producing chlorine and sodium hydroxide is described in U.S. Pat. No. 5,154,806 incorporated by reference herein in its entirety.

Figure 2:
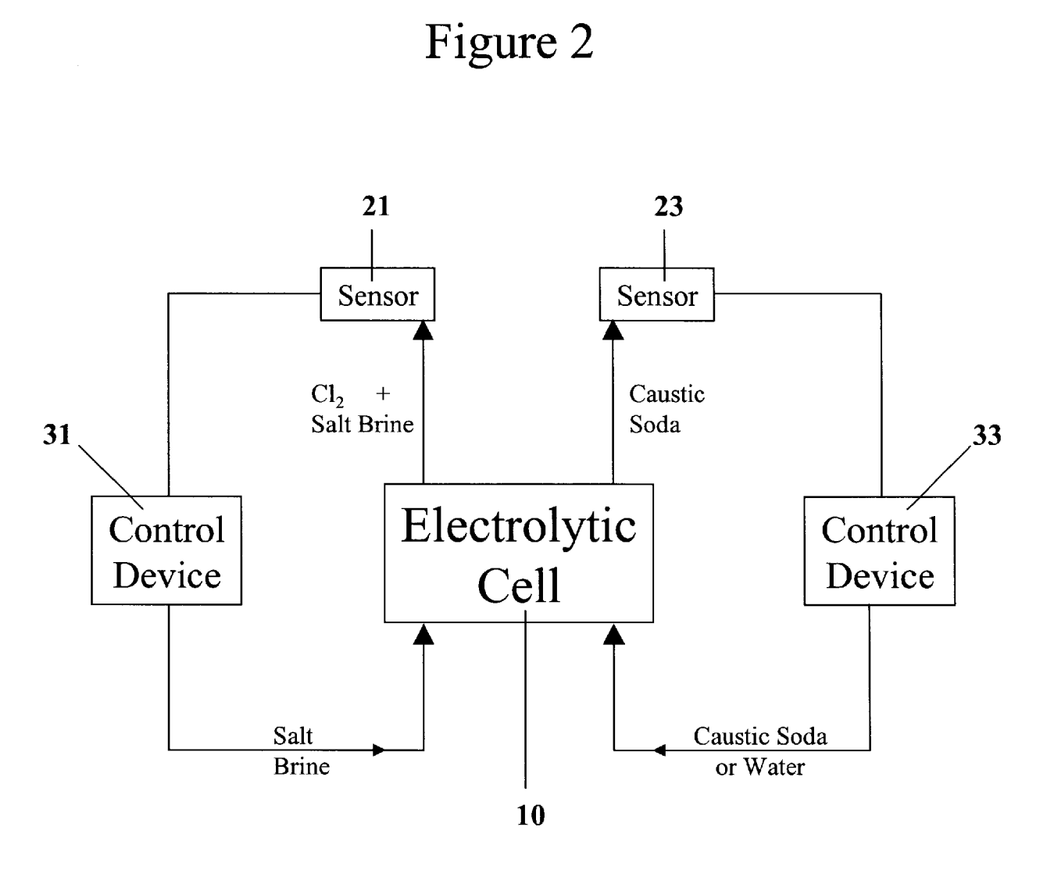
FIG. 2 is a flow diagram representing an electrolytic cell which is further equipped with a feedback device which may be used in accordance with the present invention.

The electrolytic cell 10 may additionally be equipped with sensors 21, 23 as shown in FIG. 2 for sensing the level and concentration of chlorine and sodium hydroxide produced. In turn, sensors 21, 23 may be in communication with control devices 31, 33 which control how much salt brine and caustic soda are supplied to electrolytic cell 10. Control devices 31, 33 may be in the form of a microprocessor, for instance.

Figure 3:
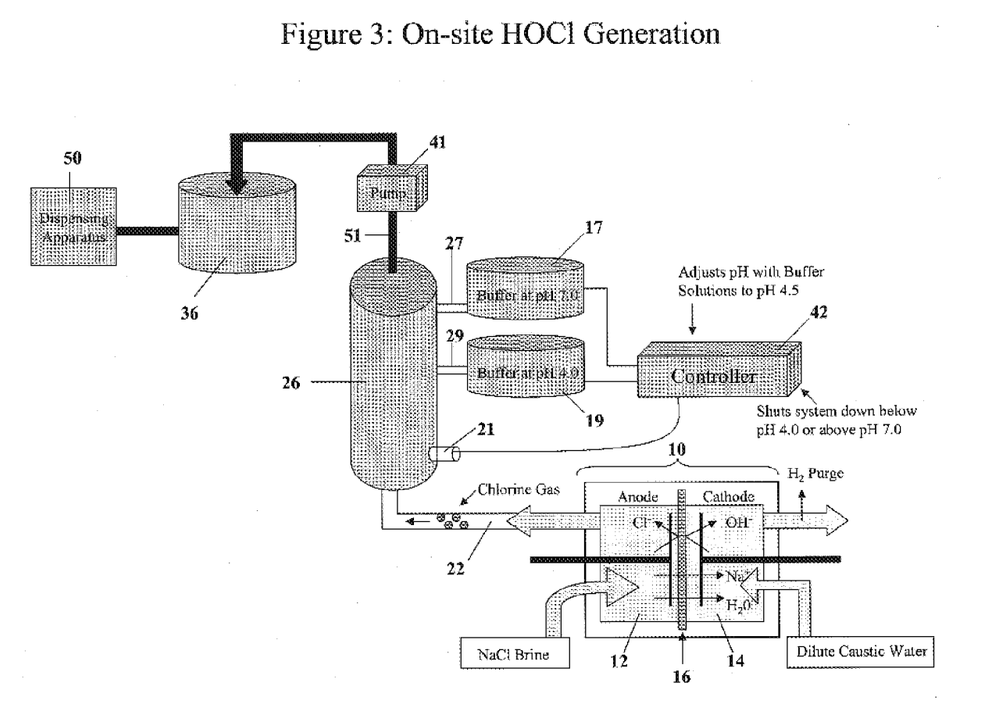
FIG. 3 is a flow diagram of one aspect of the device according to the present invention for producing and dispensing hypochlorous acid.

From this point, as illustrated in FIG. 3, chlorine gas may be transported at the site of use through a column 22 or such to another vessel or holding device 26 which includes a water based composition into which the chlorine gas is absorbed. The water based composition suitably has a pH between about 4 and 12 depending on the application for which the composition is to be employed. For instance, detergents may be more alkaline, while sanitizers may be more acidic.

The pH of the composition with which the chlorine and/or sodium hydroxide are being combined determines how the chemical composition may be employed because it determines what primary species the chlorine will exist as. For instance, at a pH of 4–7, hypochlorous acid is the most predominant species while at a pH above about 9, sodium hypochlorite is the most predominant species.

The following graph illustrates the relationship between the concentration of hypochlorous acid and the pH. The graph is adapted from Baker, R. J., *Types and Significance of Chlorine Residuals*, Journal of American Water Works Association, 1959 (51:1185).

| Solution | Amount of Chlorine present as HOCl species (%) |
|---|---|
| 4.5 | 100 |
| 5.0 | 98 |
| 6.0 | 94 |
| 7.0 | 75 |
| 8.0 | 23 |
| 9.0 | 4 |
| 10.0 | 0 |

Hypochlorous acid is known to have superior antimicrobial activity over an alkali metal hypochlorite. Therefore, for antimicrobial compositions, it may be desirable to buffer a solution to a pH of between about 4 and about 7, even more suitably between 4 and 6, and most suitably between 4 and 5. It has been found that at a pH of about 4.5, the proportion of chlorine present as hypochlorous acid appears to reach a maximum.

Sanitizers are used where desirable to reduce microbial populations such as bacteria, fungi, spores, and other biological organisms. The substantial reduction, typically five-log, in microorganisms is considered to be a sanitizing result.

Suitable buffering agents are known to those of skill in the art. Some examples of suitable buffering agents include, but are not limited to, disodium or dipotassium citrate or disodium or dipotassium phosphate with citric and phosphoric acid, for instance.

In more alkaline solutions of about a pH of 9 or higher, the alkali metal hypochlorite is the predominant species. Solutions having sodium hypochlorite present, for instance, as the predominant species may be employed as sanitizing bleaches. Solutions useful as sanitizing bleaches include a small amount of sodium hydroxide of between about 0.1% and 1.5%, and even more suitable, may include about 0.5% sodium hydroxide. Such solutions may include 5% or higher available chlorine, and more suitable about 8% or higher available chlorine.

Bleach "boosters" may also be prepared by combining 1.5% to about 10.0% available chlorine to produce sodium hypochlorite and about 0.5% sodium hydroxide.

The sodium hydroxide produced as a result of the electrolytic process may therefore be recombined with the chlorine, or it may be transported to a separate vessel 28 to be later combined with other chemical concentrates.

For instance, alkaline detergent compositions are desirable for industrial laundry processes where textile materials such as sheets, towels, wipes, garments, tablecloths, etc. are commonly laundered at elevated temperatures. For such compositions, anionic or other detergent materials, bleaches, brighteners, antiredeposition agents, and so forth for enhancing soil removal and for enhancing the appearance of the cleaned article may also be added.

Therefore, optionally, other ingredients may be added to the compositions of the present invention depending on the application for which the sanitizer and/or cleaner is being used. These compositions may also be provided to an end user in concentrate form. Examples of additives include, but are not limited to, water conditioners, solvents, surfactants and other additives from concentrates may be added as required.

These chemical concentrates may be combined in various proportions to form detergents, cleaners, sanitizers, and so forth including, but not limited to, non-foaming alkaline cleaners with and without wetting agents or surfactants, non-foaming chlorinated alkaline cleaners, heavy duty alkaline cleaners with and without wetting agents or surfactants, chlorinated heavy duty alkaline cleaners, liquid sanitizers, foaming heavy duty alkaline cleaners, and so forth. Both phosphate and non-phosphate versions may be made as well by adding phosphate or non-phosphate based materials.

FIG. 3 illustrates generally at 30, a device for producing chlorine in accordance with the present invention which is in turn employed in the production of a hypochlorous acid for use in on-site production of cleaning and/or sanitizing compositions in accordance with the present invention.

Figure 4:
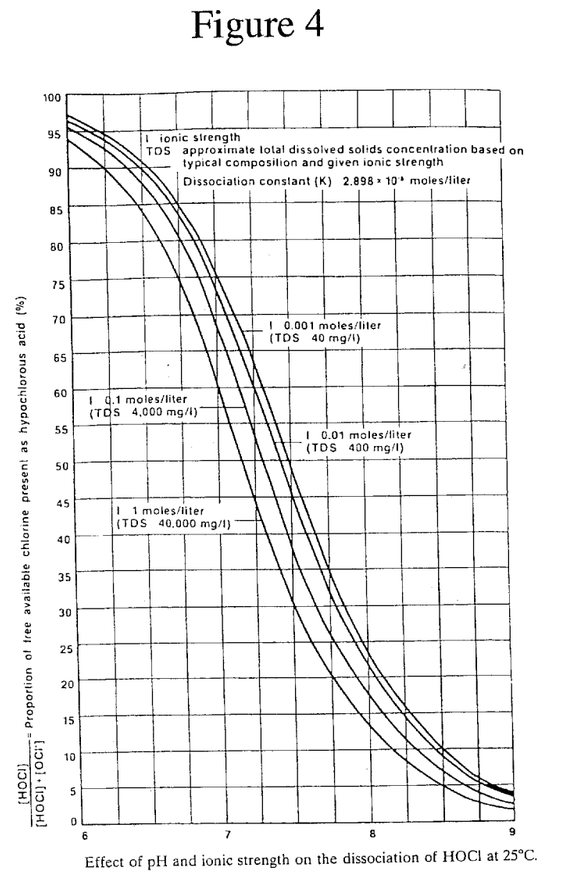
FIG. 4 is a graph illustrating the protolysis of hypochlorous acid.

An electrolytic membrane cell 10 is employed for producing chlorine gas in the anode compartment 12 of membrane cell 10 which is then transported using any delivery means known in the art through conduit 22 to vessel 26 which holds an aqueous composition. Vessels 17, 19 are in fluid communication with vessel 26. In this embodiment of the present invention vessel 17 holds a buffer at a pH of 7.0 while vessel 19 holds a buffer at a pH of 4.0. The present invention is not limited to any particular buffering composition(s) however, provided that the buffering composition(s) are capable of producing the desired pH of between 4 and 7 when mixed with chlorine. In this pH range, hypochlorous acid which is a desirable sanitizer is the primary species present. For optimum concentrations of hypochlorous acid, the pH is more suitably between about 4 and 6, and even more suitably between about 4 and 5 with the amount of hypochlorous acid reaching a maximum at a pH of about 4.5. A graph illustrating this phenomenon is shown in FIG. 4 which is reproduced from White, G. C. Handbook of Chlorination (New York: Van Nostrand-Reinhold Company, 1999, p. 1502).

Figure 7:
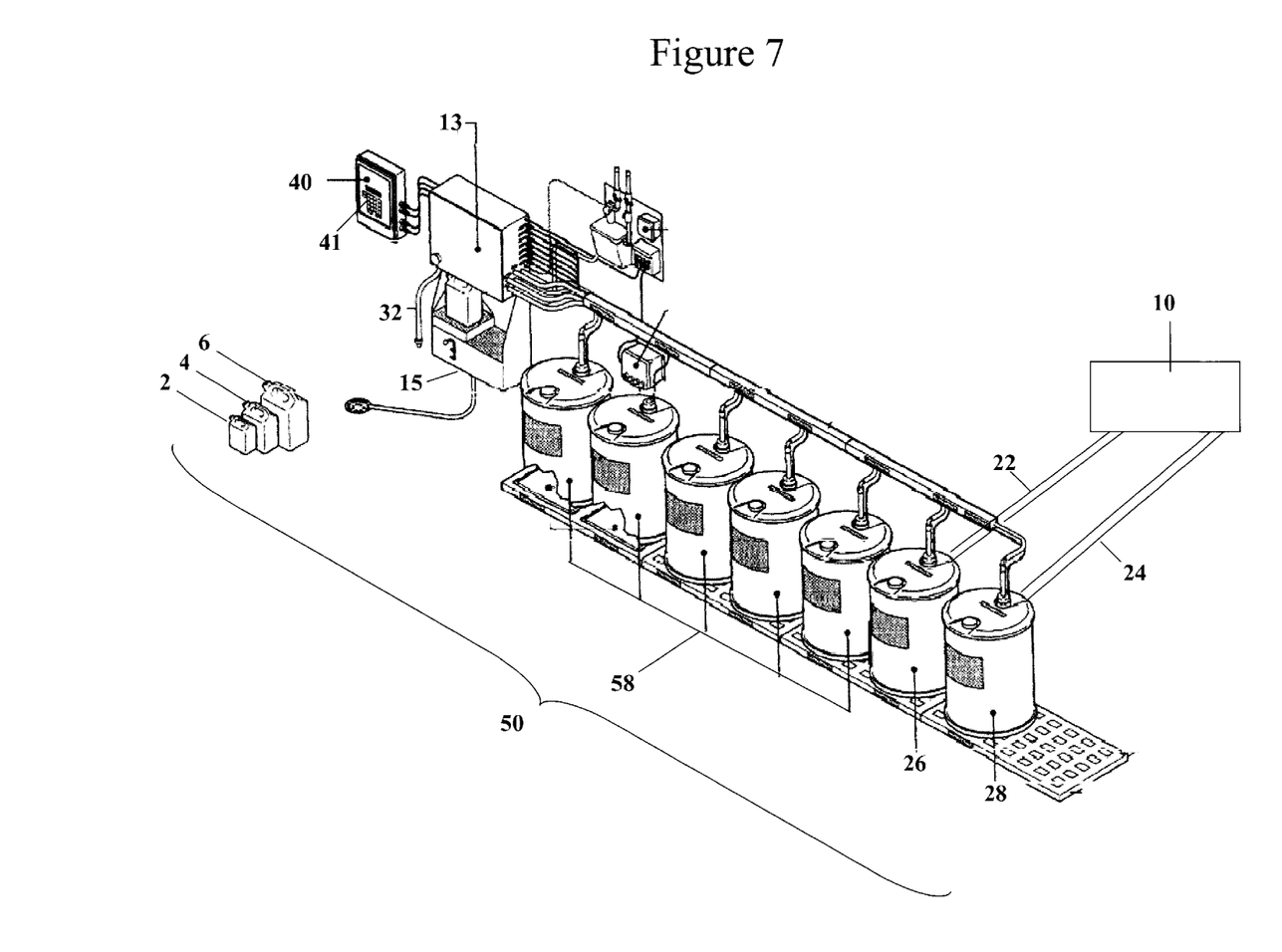
FIG. 7 is a perspective view of a dispensing apparatus which may be used in accordance with the present invention.

Microprocessor/controller 42 dispenses specified amounts of the buffering composition(s) from vessels 17, 19 depending on the pH desired. A pH probe 21 or other sensing device provides pH or other data to microprocessor/controller 42 which then shuts down delivery of the buffering compositions once the desired pH is reached. A delivery means such as pump 41 is then used to delivery the hypochlorous acid composition to vessel 36 where it may be mixed with other chemical concentrates in preparation of a final use cleaning and/or sanitizing composition. Vessel 36 may be representative of a use location clean-in-place tank, central sanitizing lines, and so forth. A dispensing apparatus 50 (not shown) which may be used to dispense the chemical concentrates such as surfactants, water conditioning agents, solvents, and so forth to vessel 36 in preparation of the final use solution is also not shown in FIG. 3. Such a dispensing apparatus may be found in U.S. Pat. No. 5,203,366 incorporated by reference herein in its entirety and is shown in FIGS. 7 and 8 and is described in detail below.

Figure 5:
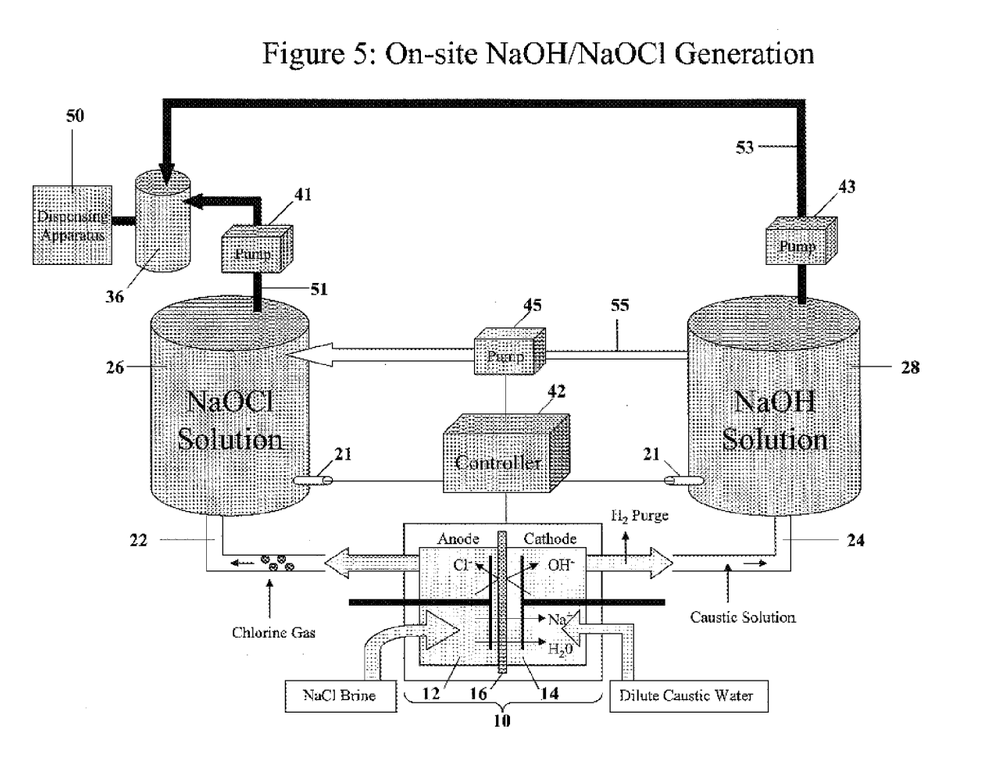
FIG. 5 is a flow diagram of one aspect of the device according to the present invention for producing and dispensing metal hypochlorite.

FIG. 5 illustrates generally at 35 one aspect of the device of the present invention for the production of chlorine and sodium hydroxide which are in turn used to produce sodium hypochlorite for use in on-site production of cleaning and/or sanitizing compositions in accordance with the present invention.

Brine is delivered to the anode compartment 12 of the electrolytic membrane cell 10 via pumping or injecting device 18. Chlorine, produced at the anode is then transported to vessel 26 while sodium hydroxide, produced at the cathode, is transported to vessel 28. The sodium hydroxide may either be transported to vessel 26 through a conduit 55 using a delivery system 45 such as a pumping device where it is admixed with chlorine to produce sodium hypochlorite and/or it may be transported through a conduit 53 by means of a delivery system 43 such as a pumping or other injecting device to vessel 36 where it is further combined with other chemical concentrates for production of a final use cleaning and/or sanitizing concentrate which may be further diluted to a final use solution. The dilution may take place in vessel 36 which may be further connected to a water supply (not shown), or it may be transported to another vessel where it is further diluted to a final use dilution.

In one embodiment, the desired pH of the composition in vessel 26 is about 9 or higher. At these pH values, the primary species is sodium hypochlorite. In this embodiment, both sodium hydroxide and chlorine are delivered to vessel 26. A pH monitor or other sensing device 21 in communication with microprocessor/controller 42 may transmit pH data to microprocessor/controller 42 which is turn starts or stops delivery of sodium hydroxide to vessel 26 depending on a predetermined pH or other solution parameters such as conductivity, which is input into microprocessor/controller 42. The amount of chlorine gas delivered may also be controlled by microprocessor/controller 42.

Microprocessor/controller 42 may be employed to direct and control the amount of sodium hypochlorite directed to vessel 36.

Optionally, a feedback device may be employed to indicate to the microprocessor/controller 42 when more sodium hydroxide or chlorine gas are required triggering microprocessor/controller to deliver more brine and/or caustic soda to the anode compartment 12 of electrolytic cell 10.

The apparatus of the present invention may also include a dispensing apparatus 50 (not shown) for dispensing other chemical concentrates including low foaming or high foaming surfactants, solvents, water conditioning agents, and so forth to vessel 36 for preparation of a final cleaning and/or sanitizing composition. The composition may further be diluted by means of a water supply, or by other means. Optionally, microprocessor/controller 42 may be configured to direct the amount of each chemical concentrate directed to vessel 36 as well as the amount of water delivered for dilution.

Figure 6:
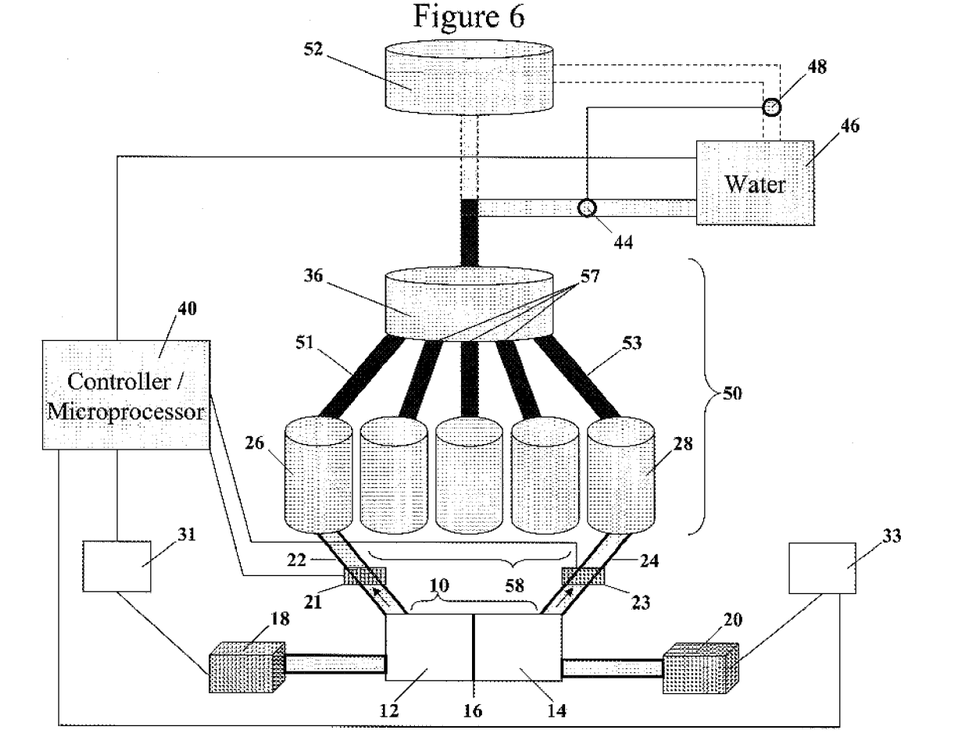
FIG. 6 is a flow diagram of an apparatus according to the present invention.

FIG. 6 illustrates generally at 15 a flow chart illustrating a device in accordance with the present invention. The device includes an electrolytic cell 10 in which chlorine is generated in cell 12 and sodium hydroxide is generated in cell 14. Chlorine gas is then transported to vessel 26 using any means known to those of skill in the art through conduit 22. Sensor 21 is employed to sense the level of chlorine being transported to vessel 26. This information is then fed back to microprocessor/controller 40 which communicates with controller 31 as to when more brine is required in cell 12 at which time microprocessor/controller 40 may also activate the pump or injecting device 18 for directing more brine to cell 12. A feedback device may also be employed in communication with microprocessor/controller 42 to direct more dilute caustic soda or water via pumping or injecting device 20 to cell 14 as required. Controller 31 can be in communication with a delivery means (not shown) such as a pump system.

Sodium hydroxide is transported in conduit 24 to vessel 28. Sensor 23 is employed to sense the level and concentration of sodium hydroxide being transported. This information is communicated by sensor 23 to microprocessor/controller 40 which then communicates with controller 33 when more caustic soda is required in cell 14.

Device 50 has a plurality of vessels 58 for holding various chemical concentrates including, but not limited to low and/or high foaming surfactants, water conditioners, solvents and so forth, for producing cleaners and/or sanitizers in accordance with the present invention at the site of use. Preferably, these concentrates are provided in the form of a liquid for ease of use. These concentrates may be transported to a common vessel 36 by any delivery means (not shown) known to those of skill in the art such as that described in U.S. Pat. No. 5,203,366 incorporated by reference herein in its entirety. The delivery system may include a pump or series of pumps in combination with an appropriate manifold 57 and valve system for transporting the concentrates from the individual vessels 58 to a central vessel 36 where the various chemical concentrates are mixed with the chlorine and/or sodium hydroxide from vessels 26, 28 also transported as described above. A predetermined recipe may be downloaded to microprocessor/controller 40 which then directs how much of each chemical concentrate is supplied to vessel 36.

The controller may be configured to activate the delivery system to deliver predetermined quantities of each of the chemical concentrates required to make the desired final composition which have been programmed based on the volumetric size of vessel 36, for instance. A flow meter having a feedback device (not shown) may be employed to communicate to the microprocessor/controller 40 when the required amounts have been delivered. At this point, the microprocessor/controller 40 may deactivate the delivery system. An alarm system may also be installed to indicate to the end user when the amount of chemical concentrate remaining in each vessel is such that they require replacement. At this point, a new vessel may be delivered.

A computer may optionally be installed and configured to calculate and download the desired formulation of final composition to the controller or microprocessor to cause the appropriate chemical concentrates and the appropriate volumes of those concentrates to be dispensed.

As described above, microprocessor/controller 40 may optionally be in communication with sensors 21, 23 which provide feedback data to the microprocessor/controller 40 as to how much chlorine and sodium hydroxide are being delivered to vessels 26, 28 as illustrated in FIG. 2 described above. The microprocessor/controller 40 may in turn be in communication with controllers 31, 33 dictating how much brine and caustic soda are directed into the electrolytic cell 10 based on the data given to the microprocessor/controller 40 from the sensors 21, 23.

A water supply 46 with a valve system 44 may be used to dilute the concentrate either in common vessel 36 or in vessel 52 in preparation of a final use solution. Microprocessor/controller 40 may activate valve 44 or valve 48 as is appropriate.

Alternatively, mixed concentrate from vessel 36 may alternatively be transported by any delivery means known in the art to vessel 52 where water from water supply 46 is provided in either vessel 36 or vessel 52 in preparation of the final diluted use solution. The vessel may be equipped with a valve which is manually operated, or is the valve system may be in communication with the microprocessor/controller 40 wherein a single button is pushed to dispense the correct predetermined amount of concentrate. Containers (not shown) for transporting the concentrate may be of any size such as 1½ gallons, 2½ gallons, 5 gallons, 55 gallon drums, and so forth may be filled from vessel 36 and transported to a large vessel where water is then filled to a mark for proper dilution.

Alternatively, when all of the concentrates have been dispensed to the central vessel 36, the valve 44 connected to the water supply 46 may be activated to dispense the desired amount of water for dilution of the mixed concentrate automatically. Optionally, a specified amount of concentrate may be dispensed to another vessel 52 as described above to which the water supply is optionally connected. The microprocessor/controller 40 may also be in communication with a valve 44 for the water supply 46 for directing how much water is required for dilution of the concentrate.

This vessel may be further connected to a clean-in-place system in an industrial facility such as a food processing plant, beverage plant, dairy operation, meat plants, rendering operations, poultry plants, and so forth.

One example of a dispensing apparatus which may be used in accordance with the device of the present invention is shown generally at 50 in FIG. 7. This particular device has a pumping station 13 and a filling station 15. The filling station may accommodate container sizes 2, 4, 6 of 1.5 gallons, 2.5 gallons and 5 gallons consecutively. Smaller containers may be accommodated as well. However, if larger containers are desired, they can be positioned outside of the filling station 15 in fluid communication with a by-pass conduit 32. In this manner, drums as large as 55 gallons or larger may be filled using the chemical cleaner dispenser.

In operation, an operator may press an "on" switch on a microprocessor/controller 40 and select the container size and product desired by simply punching in a code on keypad 41. The operator then places the container 2, 4, 6 in the filling station 15 and inserts a filling tube (not shown) into the mouth of the container. A "start" button is then pressed which begins the dispensing operation.

The microprocessor/controller 40 then directs a certain amount of each concentrate from one or more vessels 58, as well as the sodium hydroxide in vessel 28 and the chlorine composition in vessel 26 which are each connected via conduits 22, 24 to electrolytic cell 10. This concentrate may then be placed into a vessel (not shown) which can then be filled with water for dilution to a preset mark in the vessel.

FIG. 7 illustrates an alternative embodiment to that shown in FIG. 4 in which the device has more vessels 58 for dispensing a larger number of concentrates.

A dispensing apparatus such as that described above which may be used in combination with the electrolytic cell in accordance with the present invention is described in commonly assigned U.S. Pat. No. 5,203,366 incorporated by reference herein in its entirety. Other apparatuses which may find utility herein are described in commonly assigned U.S. Pat. No. 574,638, U.S. Pat. No. 5,967,202, and U.S. Pat. No. 4,976,137 each of which are incorporated by reference herein in their entirety. These devices are intended for exemplary purposes only, and other devices for producing dilute chemical compositions on-site not specifically described herein may also be used in accordance with the present invention without departing from the scope of the present invention.

Hydrogen gas, produced as a by-product of the reaction described above, may be compressed for storage and later used for power generation, or to supply a fuel cell for immediate use. A hydrogen sensor may also be optionally installed in the device. Such a sensor is described in U.S. Pat. No. 5,367,283 incorporated by reference herein in its entirety.

Although the present invention has been described with reference to particular embodiments, it should be understood that those skilled in the art may make many other modifications without departing from the spirit and scope of the invention as defined by the appended claims.

What is claimed is:

1. A process for generating cleaning compositions selected from the groan consisting of sanitizers and bleaches at the point of use, the process including a dispensing system for mixing a plurality of concentrated chemical compositions according to a predetermined recipe, the recipe providing at least one concentrated chemical composition including at least one of a buffer, a surfactant, a solvent or a water conditioning agent and combining said concentrated chemical composition with chlorine, sodium hydroxide, or mixture thereof, wherein said process employs an on-site generator of chlorine and sodium hydroxide by electrolysis of a sodium chloride solution, wherein the sanitizers are formed at a pH of about 4 to about 7, and the bleaches are formed at a pH of about 9 or higher by combining sodium hydroxide and chlorine formed during said process.

2. The process of claim 1 wherein said dispensing system has a delivery system for delivering chlorine.

3. The process of claim 2 wherein said chlorine is delivered into a liquid chemical composition having a pH of about 4.5.

4. The process of claim 1 wherein said chlorine is delivered into a liquid chemical composition having a pH of about 4 to about 5.

5. The process of claim 1 wherein said dispensing system has a delivery system for delivering sodium hydroxide.

6. The process of claim 1 wherein said chlorine and said sodium hydroxide are delivered to a common vessel to produce a chemical composition having a pH of about 9 or greater.

7. The process of claim 1 wherein said concentrated chemical composition is diluted with water at a ratio of up to 1:400.

8. The process of claim 1 wherein said on-site generator is an electrolytic cell.

9. The process of claim 8 wherein said electrolytic cell is a diaphragm cell, a bipolar diaphragm cell, a membrane cell or a mercury cell.

10. The process of claim 8 wherein said electrolytic cell is a membrane cell.

11. The process of claim 1 wherein said bleaches are formed by combining sodium hydroxide formed during said process with said chlorine fanned during said process, wherein said sodium hydroxide is combined in said bleach at a concentration of about 0.1 wt-% to about 1.5 wt-% and said chlorine is combined in said bleach at a concentration of about 5 wt-% or more available chlorine.

12. The process of claim 11 wherein said sodium hydroxide in said bleach is about 0.5 wt-% and said available chlorine in said bleach is about 1.5 wt-% to about 10 wt-%.

13. A process for manufacturing cleaning solutions comprising the steps of:
   a) generating chlorine, sodium hydroxide, or a mixture thereof using an electrolytic coil;
   b) collecting chlorine in a first vessel and sodium hydroxide in a second vessel;
   c) providing a plurality of concentrated chemical compositions in a plurality of vessels, each vessel storing one of said plurality of concentrated chemical compositions;
   d) selecting a predetermined cleaning composition selected from the group consisting of sanitizers at a pH of about 4 to about 7 and bleaches at a of about 9 or higher to be produced using a microprocessor controller, the predetermined cleaning composition including a predetermined amount of at least one of said plurality of concentrated chemical compositions and a predetermined amount of at least one of chlorine, sodium hydroxide, or mixture thereof; and
   e) directing said predetermined amount of said at least one of said plurality of concentrated chemical compositions, and said predetermined amount of at least one of said chlorine, sodium hydroxide, or mixture thereof into a vessel thereby generating a desired cleaning composition.

14. The process of claim 13 wherein said electrolytic cell comprises an anode compartment, a cathode compartment, and a membrane separating the two compartments.

15. The process of claim 13 wherein said chlorine gas enters a solution buffered to a pH of about 4.5.

16. The process of claim 15 wherein said solution is buffered with mono-, di-, or tri-, sodium or potassium phosphates, sodium or potassium citrates, or mixtures thereof.

17. The process of claim 13 wherein said chlorine gas enters a solution buffered to a pH of about 4 to about 5 producing hypochlorous acid as a primary species.

18. The process of claim 17 wherein said solution is buffered with sodium citrate, potassium citrate, or mixture thereof.

19. The process of claim 13 wherein before step 3) said chlorine and said sodium hydroxide are mixed and said resultant composition has a pH of greater than about 9 producing sodium hypochlorite as the primary species.

20. The process of claim 13 further comprising the step of diluting said cleaning composition with water.

21. The process of claim 13 wherein said predetermined amount of sodium hydroxide delivered is about 0.1 wt-% to about 1.5 wt-% and said predetermined amount of available choline delivered is about 5 wt-% or greater.

22. The process of claim 21 wherein said predetermined amount of sodium hydroxide delivered is about 0.5 wt-% and said predetermined amount of available chlorine delivered is about 1.5 wt-% to about 10 wt-%.

23. An apparatus for the preparation of multi-component chemical cleaning compositions at the point of use comprising:
   a) at least one electrolytic cell for generating at least one of chlorine, sodium hydroxide or mixture thereof;
   b) a plurality of concentrated chemical compositions in a plurality of vessels, each vessel storing one of said plurality of concentrated chemical compositions;
   c) a controller for selecting a predetermined amount of at least one of a plurality of concentrated chemical compositions; and
   d) a delivery system in communication with said controller wherein said delivery system delivers said predetermined amount of said at least one of sodium hydroxide, chlorine, or mixture thereof and said predetermined amount of at least one of said plurality of chemical compositions to a common vessel, said combination of sodium hydroxide, chlorine, and said plurality of chemical compositions are combined to form at least one of a sanitizer having a pH of about 4 to about 7, a bleach having a pH of about 9 or greater, or both.

24. The apparatus of claim 23 further comprising a computer configured to download the desired cleaning composition to the controller.

25. The apparatus of claim 23 wherein at least one of said plurality of chemical compositions has a pH of about 4.5.

26. The apparatus of claim 23 wherein at least one of said plurality of chemical compositions has a pH of about 4 to about 5 and said chlorine is delivered to said composition having a pH of about 4 to about 5.

27. The apparatus of claim 23 having an additional delivery system and an addition vessel wherein said additional delivery system delivers chlorine and sodium hydroxide to said additional vessel to produce a mixture having a pH of about 9.

28. The apparatus of claim 23 wherein said electrolytic cell is a diaphragm cell, a bipolar diaphragm cell, a membrane cell or a mercury cell.

29. The apparatus of claim 23 wherein said predetermined amount of sodium hydroxide delivered is about 0.1 wt-% to about 1.5 wt-% and said predetermined amount of available chlorine delivered is about 5 wt-% or greater.

30. The apparatus of claim 23 wherein said predetermined amount of sodium hydroxide delivered is about 0.5 wt-% and said predetermined amount of available chlorine delivered is about 1.5 wt-% to about 10 wt-%.

* * * * *